United States Patent [19]
Cawse et al.

[11] Patent Number: 6,107,437
[45] Date of Patent: Aug. 22, 2000

[54] CURING AGENTS

[75] Inventors: John Leslie Cawse, Castle Camps; Mark Whiter, Saffron Walden, both of United Kingdom

[73] Assignee: Hexcel Corporatioin, Pleasanton, Calif.

[21] Appl. No.: 09/162,074

[22] Filed: Sep. 28, 1998

[30] Foreign Application Priority Data

Oct. 2, 1997 [EP] European Pat. Off. .............. 97307793

[51] Int. Cl.⁷ ..................................... C08G 59/68
[52] U.S. Cl. .............................. 528/94; 540/470; 540/480
[58] Field of Search ............................... 528/94; 540/470, 540/480

[56] References Cited

U.S. PATENT DOCUMENTS

| | | | |
|---|---|---|---|
| 3,756,984 | 9/1973 | Klaren et al. .............................. | 528/94 |
| 3,920,678 | 11/1975 | Butula ..................................... | 260/309 |
| 4,066,625 | 1/1978 | Bolger .................................... | 260/59 R |
| 5,169,473 | 12/1992 | Bertram et al. .......................... | 156/307 |

FOREIGN PATENT DOCUMENTS

| | | |
|---|---|---|
| 254806 | 5/1989 | Czech Rep. . |
| 01117866 | 5/1989 | Japan . |

OTHER PUBLICATIONS

Ashcroft, W.R., "Curing Agents For Epoxy Resins," *Chemistry and Technology of Epoxy Resins*, pp. 36–71 (1992).

*Primary Examiner*—Robert Dawson
*Assistant Examiner*—D. Aylward
*Attorney, Agent, or Firm*—Hexcel Corporation

[57] ABSTRACT

Curing agents for epoxy resins are provided in which an imidazole is substituted on the nitrogen atom by a long chain group. This provides greater latexing (stability) at ambient temperatures without adversely affecting curing properties at temperatures of 50° C. upwards. Those components in which the chain is substituted by a hydroxy group on the 2 position are particularly preferred and are novel compounds.

4 Claims, No Drawings

CURING AGENTS

BACKGROUND OF THE INVENTION

1. Field of the Invention

This invention relates to curing agents suitable for use for curing epoxy resins to form storage stable epoxy resin compositions containing the curing agents. The present invention further relates to methods of curing epoxy resin compositions with the curing agents.

2. Description of Related Art

Epoxy resins are very widely used as matrices for fiber-reinforced composites. Such composites are used in industrial and aerospace applications as structural components, and for electronic circuit boards and in many other areas. Epoxy resins are also widely used as structural adhesives in the form of so-called film adhesives and as pastes and liquids.

There are a number of different reaction mechanisms which can be used to cure epoxy resins. These are well known in the art and are described in, for example, "The Chemistry and Technology of Epoxy Resins" by B. Ellis, Blackie Academic Press, Glasgow 1993, Chapter 2 "Curing Agents for Epoxy Resins." One known mechanism involves reacting the epoxy with a stoichiometric amount of an active hydrogen containing compound, for example a difunctional primary amine with each epoxy terminal reacting with a corresponding active hydrogen containing moiety. Another mechanism involves the utilization of an agent which behaves as an initiator for the ring opening polymerization of the epoxide ring. Thus the purpose of the initiator is to activate a terminal epoxide moiety on the epoxy resin by breaking open the epoxide ring and forming an unstable intermediate which can then react with a second epoxide terminal. Thus in this reaction mechanism one epoxide terminal effectively reacts with another epoxide terminal without there being needed a separate cross-linking molecule. The most common initiator is a tertiary amine of which imidazoles are particularly well known.

Thus imidazoles are known as very effective, highly active curing agents for epoxy resins. Many examples are commercially available, for instance, 2-methyl imidazole, 2-ethyl-4-methyl imidazole, 2-phenyl imidazole and 1-benzyl-2-methyl imidazole.

Generally, epoxy resins and corresponding curing agents are packaged in separate pots to avoid premature curing on storage. In use the cured composition is formed by mixing ingredients from the respective pots. However, some one pot epoxy compositions are known in the art. Examples of such compositions are compositions comprising the epoxy resin and imidazole curing agents. However, although these compositions are ideal for bringing about the rapid cure of epoxies at relatively low temperatures, the pot life of such one pot compositions is short, for example, on the order of one to three days at room temperature.

Conversely, other known one pot compositions have longer pot lives on the order of one or more weeks but these known compositions are disadvantageous in view of the high cure temperature that is required which is typically well over 100° C.

The compounds 1-benzyl-2-methyl imidazole and 2-methyl imidazole are known curing agents for epoxides. However, when formulated in one pot compositions, these curing agents typically exhibit a pot life of only two to three days at room temperature.

Thus, although many imidazoles are ideal for bringing about the rapid cure of epoxy resins at relatively low temperatures, the combination of imidazole and epoxy resin must be used very quickly owing to the poor stability of the formulations.

In certain applications it is very important to have an epoxy resin formulation which will cure rapidly at relatively low temperature, for example, 60 to 80° C., but which will nevertheless maintain an acceptably long out-life on storage at room temperature. Examples of such applications are in the form of very large pre-preg parts, for instance in the fabrication of large structures in the transportation industry. It is often essential in such cases to use the lowest practicable cure temperature to avoid the need for very large ovens. Arranging a simple awning over the laid-up structure and directing hot air at the surfaces to be cured may then effect cure. Because of the length of time taken to lay up the pre-preg sheets, a long out-life is needed, often several days to a week or more.

It is found that in practice that the existing imidazole curatives have sufficient latency to allow their use in such low temperature, long out-life applications. Whilst cure can often be achieved at the required low temperature, the latency is usually inadequate, often on the order of two to three days. An out-life of at least one week and preferably at least two weeks would be required in many cases. Conversely, imidazole curatives are available which possess latencies of one or more weeks, but then the minimum useful cure temperature will be much higher, and typically well over 100° C.

In U.S. Pat. No. 3,756,984 there are described reaction products of glycidyl esters and imidazoles, particularly those in which there is a tertiary or quaternary carbon in the carboxylic acid from which the glycidyl ester is derived. No long chain alkyls are described as the chain is interrupted by an ester grouping. The emphasis is on increasing solubility of the products. There is no suggestion of the advantages of $C_{12}$–$C_{18}$ chains.

SUMMARY OF THE INVENTION

The technical problem with which the present invention is concerned is to provide an imidazole type curing agent for epoxy resin compositions, which will allow cure to be carried out at comparatively low temperatures while at the same time maintaining an advantageous latency or out-life of the epoxy composition.

According to the invention there are provided as epoxy curing agents compounds of the formula

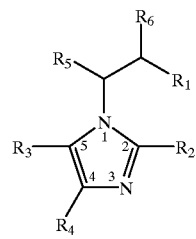

wherein $R_1$ is $C_6$ to $C_{24}$ saturated or unsaturated straight or branched chain alkyl or cycloaliphatic group, or may with $R_5$ form a ring; $R_1$ may also be an imidazole having the formula

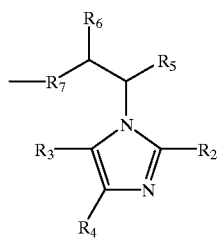

wherein $R_7$ is $C_6$ to $C_{24}$ straight or branched chain alkyl, cycloaliphatic or alkylene;

$R_2$ is H, $C_1$ to $C_{18}$ alkyl, aryl or substituted aryl;

$R_3$ and $R_4$ may be the same or different and may be H, $C_1$ to $C_3$ alkyl, aryl or substituted aryl, —$CH_2OH$, —CN, Cl or may together form a ring;

$R_5$ is H or together with $R_1$ forms a non-aromatic ring;

$R_6$ is H or OH or $C_7$ to $C_{25}$ straight or branched chain alkyl.

$R_1$ can be substituted with groups of low polarity for example alkyl, alkenyl, ether or ester.

Preferably $R_6$ is OH. Hydroxy substituted compounds have advantages over simple N-alkyl imidazoles. Most preferably $R_6$ is OH and $R_1$ is $C_{14-18}$ linear alkyl.

The above discussed and many other features and attendant advantages will become better understood by reference to the following detailed description.

DETAILED DESCRIPTION OF THE INVENTION

The curing agents of the present invention have the formula

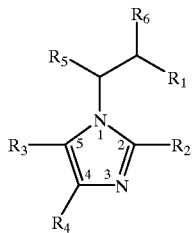

wherein $R_1$ is $C_6$ to $C_{24}$ saturated or unsaturated straight or branched chain alkyl or cycloaliphatic group, or may with $R_5$ form a ring; $R_1$ may also be an imidazole having the formula

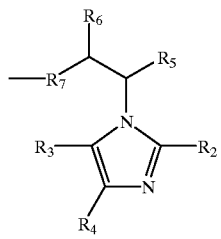

wherein $R_7$ is $C_6$ to $C_{24}$ straight or branched chain alkyl, cycloaliphatic or alkylene;

$R_2$ is H, $C_1$ to $C_{18}$ alkyl, aryl or substituted aryl;

$R_3$ and $R_4$ may be the same or different and may be H, $C_1$ to $C_3$ alkyl aryl or substituted aryl, —$CH_2OH$, —CN, Cl or may together form a ring;

$R_5$ is H or together with $R_1$ forms a non-aromatic ring;

$R_6$ is H or OH or $C_7$ to $C_{25}$ straight or branched chain alkyl.

In selecting $R_1$–$R_7$, the tendency to solubility in an epoxy system should be considered. Substituents which in themselves or in combination with other substituents create high solubility in the system are probably undesirable. Thus compounds in which $R_6$ is H or alkyl tend to a higher solubility which is a reason for preferring $R_6$ as OH.

The known N-alkyl imidazoles have been suggested for possible pharmacological purposes but there has been no proposal as epoxy curing agents.

The hydroxy compounds $R_6$=OH have advantages over known N-alkyl imidazoles in that the latter tend to be liquids or low melting solids, making them difficult to isolate and inconvenient to use in formulations. For example, N-dodecyl imidazole is a liquid at ambient temperature and N-octadecyl imidazole is a solid with a melting point of only 47° C. (Ref: A de Savignac et al., Eur. J. Med. Chem. (1990), 25, 449–454). By contrast, the compounds of the current invention may be readily isolated and purified as well-defined solids with melting points in the region of 50 to 100° C.

Without wishing to be bound by theory, it is believed that the length of the carbon chain in the compounds used in the invention influences the solubility of the curing agents in the epoxy resin and thereby influences the latency period. Thus it is believed that longer alkyl chains confer greater latency. Surprisingly, as the alkyl chain length gets longer, there is no great decrease in intrinsic reactivity of the curing agents. This is contrary to what one skilled in the art would have expected. Again, without wishing to be bound by theory, it is believed that the imidazole component of the adduct is responsible for determining the reactivity of the curing agent. Thus it has been demonstrated that adducts of the invention comprising imidazole or 2-methyl imidazole are more reactive than, for example, adducts of the invention comprising 2-benzyl-4-methyl imidazoles.

By appropriate choices of the epoxy alkyl compound and the imidazole compound the activity and latency of the compounds of the invention may be tailored to a wide range of requirements.

Thus compounds in which the imidazole ring is unsubstituted or 2-alkyl substitutes tend to be more reactive than aryl substituents such as benzyl. Similarly, the selection of the chain length for $R_1$ or $R_7$ tends to adjust the latency properties. Longer carbon chains influence solubility in the epoxy resin. Compounds where $R_1$ is $C_{14}$ to $C_{18}$ linear alkyl are preferred.

A further advantage of the curing agents where $R_6$ is OH is that they can be produced relatively easily by reaction of an imidazole and a long chain epoxy alkyl compound. A monoepoxy compound will produce preferred compounds in which $R_7$ is the simple residue of the epoxy compound while a diepoxy will produce compounds having two imidazole rings.

For those curing agents where $R_1$ and $R_5$ form a ring, the ring should have from 4 to 24 carbon atoms (i.e., $C_4$ to $C_{24}$) and preferably from 4 to 12 carbon atoms. Exemplary curing agents where $R_1$ and $R_5$ form a ring have the following formulas:

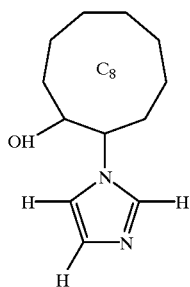

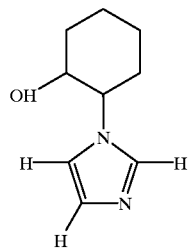

Another exemplary compound where $R_1$ and $R_5$ form a ring is formed by reacting imidazole with cyclododecane epoxide. The resulting curing agent is shown below where the $R_1/R_5$ ring has 12 carbon atoms.

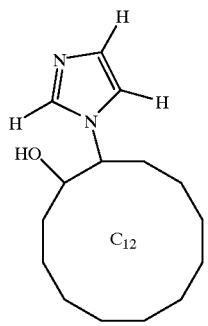

Therefore, from another point of view, the preferred compounds of the invention are the reaction products of imidazoles particularly the imidazoles known as curing agents for epoxy resins with epoxy alkyl compounds containing alkyl chains of 7 to 25 carbon atoms.

Thus in selecting the appropriate substituents for the groups in formula I, due account can be taken of the known imidazole compounds and their substituents.

Typical epoxy alkyl components which can be employed are 1,2-epoxy decane, 1,2-epoxy dodecane, 1,2-epoxy tetradecane, 1,2-epoxy hexadecane, 1,2-epoxy octadecane, 1,2,7,8-diepoxy octane, cyclododecane epoxide, cyclohexadecane epoxide and 1,2,5,6-diepoxy cyclooctane.

Imidazoles which may be used to form adducts have the formula

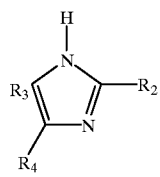

where $R_2$ is H, $C_1$ to $C_{18}$ alkyl, aryl or substituted aryl; and $R_3$ and $R_4$ are the same or different and may be H, $C_1$ to $C_3$ alkyl, aryl or substituted aryl, —$CH_2OH$, —$CN$, Cl or may together form a ring.

Examples of imidazoles or imidazole derivatives which can be used for preparing the adducts of the invention are imidazole, 2-methylimidazole, 2-ethylimidazole, 2-propylimidazole, 2-ethyl-4-methylimidazole, 4-(hydroxymethyl) imidazole, 2-phenylimidazole, 2-benzyl-4-methylimidazole and benzimidazole but the invention is not limited to these specific examples. As stated earlier, those skilled in the art are aware of imidazoles and substituted imidazoles which are effective as curing agents for epoxy resins.

These preferred curing agents of the invention can be prepared by heating the imidazole and the epoxy alkane together in the melt state or in a suitable organic solvent. Preferred solvents include acetone, ethylacetate, toluene, cyclohexane, dipolar aprotic solvents such as dimethylformamide and N-methyl pyrrolidone, and petroleum ethers. When mixtures of imidazoles are used with a diepoxy, $R_2$ to $R_6$ in Formula I may be different from the $R_2$ to $R_6$ groups shown for $R_1$ when $R_1$ is an imidazole.

The epoxy resins which can be used with the curing agents of this invention are not limited and include both liquid and solid types. For example, suitable epoxy resins including the following: the glycidyl ethers of bisphenol A and bisphenol F and of other polyhydric phenols such as resorcinol and hydroquinone; the diglycidyl ether of 9,9-bis (4-hydroxyphenyl) fluorenes, the glycidyl ethers of the condensation products of aldehydes and ketones with mono- and polyhydric phenols, the group of compounds formed by condensing phenol or cresol with formaldehyde, i.e., the phenol/cresol novolaks; and the glycidyl derivatives of various aminophenols such as 3-aminophenol and 4-aminophenol.

A specific example of a suitable resin is the triphenol formed by condensing acetone and methyhydroquinone as described in U.S. Pat. No. 5,606,006.

The curing agent will generally be used in from 0.1 to 30 parts by weight of agent to 100 parts by weight of epoxy resin.

As mentioned above, the curing agents of this invention when used in one pot heat curable epoxy compositions allow for advantageously long pot lives and advantageously low curing temperatures. For example, the compositions of the invention can be cured at temperatures in the range of 50–100° C. preferably 50 to 80° C.

While the novel curing agents described herein can be used in epoxy compositions to provide both greater stability at ambient temperatures and low temperature curing, i.e., curing at 50° to 100° C., they are not limited to these uses. For example, the compounds disclosed herein can be used advantageously at curing temperatures in the range of 50–180° C. In such cases, the necessary cure times will decrease accordingly.

The invention will now be illustrated by the following examples:

EXAMPLE 1

1,2-epoxyoctadecane (1 g) and imidazole (0.254 g) were charged to a 25 ml conical flask and heated and stirred in cyclohexane (5 ml) to give a clear solution. The mixture was held at reflux for four hours before allowing to cool. The resulting off-white precipitate was filtered and washed with cyclohexane before being dried under vacuum. Yield =83.7% of curing agent where $R_1=C_{16}$ straight chain aliphatic, $R_2$ to $R_5$=H and $R_6$=OH.

| Chemical shift δ ppm | Number of Protons | Proton Identification |
|---|---|---|
| 1.01 | 3 | Terminal methyl protons on alkyl chain C$_4$ from imidazole nitrogen |
| 1.40–1.60 | 2 | Methylene protons on alkyl chain C$_3$ from imidazole nitrogen |
| 2.22 | 3 | Methyl group protons on 2 position of imidazole |
| 3.60–3.85 | 3 | Two C$_1$ and protons C$_2$ proton multiplet |
| 5.75 (broad) | 1 | Hydroxyl proton on C$_2$ |
| 6.64 | 1 | Proton on 5 position of imidazole |
| 6.80 | 1 | Proton on 4 position of imidazole |

EXAMPLE 2

1,2-epoxydodecane (1 g) and 2-methylimidazole (0.445 g) were melted together in a 25 ml conical flask on a hotplate set at 200° C. Within one minute the molten mixture rapidly changed from colorless to an orange color and was allowed to cool. On cooling the mixture solidified to an off-white solid. Yield=100% of curing agent where R$_1$=C$_{10}$ straight chain aliphatic, R$_2$=methyl, R$_3$ to R$_5$=H and R$_6$=OH.

Melting point 89–90° C.

NMR

| Chemical shift δ ppm | Number of Protons | Proton Identification |
|---|---|---|
| 0.85–0.95 | 3 | Terminal methyl protons on alkyl chain C$_4$ from imidazole nitrogen |
| 1.20–1.40 | 18 | Methylene protons on alkyl chain C$_3$ from imidazole nitrogen |
| 2.22 | 3 | Methyl group protons on 2 position of imidazole |
| 3.65–3.85 | 3 | Two C$_1$ and protons one C$_2$ proton multiplet |
| 5.4 (broad) | 1 | Hydroxyl proton on C$_2$ |
| 6.62 | 1 | Proton on 5 position of imidazole |
| 6.82 | 1 | Proton on 4 position of imidazole |

In a similar fashion to Examples 1 and 2 a range of compounds was prepared from various epoxy alkanes and various imidazoles as set forth in Table 1.

The resulting products were used to cure epoxy resin as desired in the following Example.

EXAMPLE 3

A number of compounds produced as above were each mixed with an epoxy resin in an amount of 0.29 nmol of curing agent to 1 g of LY556 epoxy resin (diglycidyl ether of Bisphenol A, product of Ciba-Geigy).

Also included for comparison were imidazole and 2-methyl imidazole.

The percentage cure was determined by heating the mixture at 60° C. for 10 hours followed by determining the degree of cure using differential scanning calorimetry (DSC). The latency was determined at 22° C. by observing the time at which the resin ceased to be liquid.

TABLE 1

Latency of compounds of the present invention compared with imidazole and 2-methyl imidazole

| 1,2-epoxy moiety | imidazole moiety | % cure at 60° C. | latency @ 22° C., days |
|---|---|---|---|
| none | imidazole | 67.7 | 1–2 |
| dodecane | imidazole | 77.7 | 7 |
| tetradecane | imidazole | 76.6 | 10 |
| hexadecane | imidazole | 78.5 | 18 |
| octadecane | imidazole | 80.4 | 21 |
| none | 2-methylimidazole | 79.6 | 1–2 |
| dodecane | 2-methylimidazole | 83.8 | 10 |
| tetradecane | 2-methylimidazole | 85.8 | 14 |
| hexadecane | 2-methylimidazole | 85.0 | 31 |
| octadecane | 2-methylimidazole | 83.9 | 32 |

As can be seen from the above Table 1, the compounds of this invention, when formulated with an epoxy resin, produce formulations which have a degree of cure at least as good as the unmodified imidazoles, but show greatly enhanced latency.

EXAMPLE 4

An additional exemplary curing agent was prepared in the same manner as Example 1 except that a mixture of aliphatic olefins having from 20 to 24 carbon atoms and a single terminal epoxide were used in place of 1,2-epoxyoctadecane. The resulting curing agent was found to have suitable latent curing properties.

What is claimed is:

1. A curing agent for epoxy resins of the formula

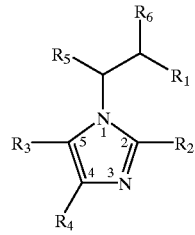

wherein R$_1$ is C$_6$ to C$_{24}$ saturated or unsaturated straight or branched chain alkyl or cycloaliphatic group, or may with R$_5$ form a ring; R$_1$ may also be an imidazole having the formula

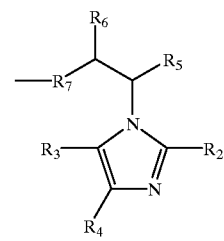

wherein R$_7$ is C$_6$ to C$_{24}$ straight or branched chain alkyl, cycloaliphatic or alkylene;

R$_2$ is H, C$_1$ to C$_{18}$ alkyl, aryl or substituted aryl;

R$_3$ and R$_4$ may be the same or different and may be H, C$_1$ to C$_3$ alkyl aryl or substituted aryl, —CH$_2$OH, —CN, Cl or may together form a ring;

$R_5$ is H or together with R1 forms a non-aromatic ring; and $R_6$ is OH.

2. A compound according to claim 1 wherein $R_1$ is $C_{14}$ to $C_{18}$ linear alkyl.

3. An epoxy composition comprising a curable epoxy composition and a curing agent as defined in claim 1.

4. A method for curing an epoxy resin comprising the step of adding to uncured epoxy resin an amount of curing agent set forth in claim 1 which is sufficient to provide for curing of said uncured epoxy resin.

* * * * *